United States Patent
Wang et al.

(10) Patent No.: US 9,682,178 B2
(45) Date of Patent: Jun. 20, 2017

(54) IMPLANTABLE MEDICAL DEVICES FABRICATED FROM POLYMERS WITH RADIOPAQUE GROUPS

(75) Inventors: Yunbing Wang, Sunnyvale, CA (US); David C. Gale, Kennesaw, GA (US); Vincent J. Gueriguian, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1360 days.

(21) Appl. No.: 13/562,009

(22) Filed: Jul. 30, 2012

(65) Prior Publication Data
US 2012/0303114 A1    Nov. 29, 2012

Related U.S. Application Data

(62) Division of application No. 11/799,354, filed on Apr. 30, 2007, now abandoned.

(51) Int. Cl.
*A61F 2/82*    (2013.01)
*A61L 31/18*    (2006.01)
*A61L 31/06*    (2006.01)

(52) U.S. Cl.
CPC ........ *A61L 31/18* (2013.01); *A61L 31/06* (2013.01)

(58) Field of Classification Search
CPC ..................... A61F 2/06; A61F 2/82
USPC ................. 623/1.11–1.48; 424/9.1
See application file for complete search history.

(56) References Cited

U.S. PATENT DOCUMENTS

| | | | |
|---|---|---|---|
| 5,399,666 A * | 3/1995 | Ford | C08G 63/08 525/413 |
| 6,426,145 B1 * | 7/2002 | Moroni | A61K 49/0442 424/9.4 |
| 6,475,477 B1 | 11/2002 | Kohn et al. | |
| 7,935,143 B2 * | 5/2011 | Wang | A61L 31/18 427/2.24 |
| 8,062,465 B1 * | 11/2011 | Huang | A61F 2/95 156/294 |
| 2003/0004563 A1 | 1/2003 | Jackson et al. | |
| 2003/0086958 A1 | 5/2003 | Arnold et al. | |
| 2003/0224033 A1 | 12/2003 | Li et al. | |
| 2006/0095122 A1 * | 5/2006 | Pacetti | A61L 31/10 623/1.46 |
| 2006/0167538 A1 * | 7/2006 | Rucker | A61F 2/04 623/1.25 |
| 2006/0292077 A1 | 12/2006 | Zhao | |
| 2008/0269874 A1 * | 10/2008 | Wang | A61L 31/06 623/1.34 |
| 2010/0290995 A1 * | 11/2010 | Pathak | A61K 49/0442 424/9.1 |

(Continued)

FOREIGN PATENT DOCUMENTS

WO    WO 02/096967    12/2002
WO    WO 2006/020616    2/2006

OTHER PUBLICATIONS

ScienceDirect Biomaterials 28 (2007) 3182-3187 on imparting radiopacity to a poly(urethane urea0.*

(Continued)

*Primary Examiner* — Suzette J Gherbi
(74) *Attorney, Agent, or Firm* — Squire Patton Boggs (US) LLP (57) ABSTRACT

Implantable medical devices comprising radiopaque star-block copolymers.

14 Claims, 3 Drawing Sheets

FIG. 4A (56) References Cited

U.S. PATENT DOCUMENTS

| | | | |
|---|---|---|---|
| 2011/0177150 A1* | 7/2011 | Pathak | A61K 35/12 424/422 |
| 2012/0024460 A1* | 2/2012 | Huang | A61F 2/95 156/86 |
| 2012/0024474 A1* | 2/2012 | Huang | A61F 2/95 156/308.2 |

OTHER PUBLICATIONS

Synthesis of an X-ray opaque biodegradable copolyester by chemical modification of poly (e-caproactone) 27 (2006) 4948-4954.*
International Search Report for PCT/US2008/059475, mailed Sep. 2, 2009, 7 pgs.
James et al. "On imparting radiopacity to a poly(urethane urea)", Biomaterials 28, pp. 3182-3187 (2007).
Nottelet et al., "Synthesis of an X-ray opaque biodegradable copolyester by chemical modification of poly (ϵ-caprolactone)", Biomaterials 27, pp. 4948-4954 (2006).
Wang et al., "Polyethylene-Poly(L-lactide) Diblock Copolymers: Synthesis and Compatilization of Poly(L-lactide)/Polyethylene Blends", Journal of Polymer Science. vol. 39, pp. 2755-2766 (2001).

* cited by examiner

IMPLANTABLE MEDICAL DEVICES FABRICATED FROM POLYMERS WITH RADIOPAQUE GROUPS

RELATED APPLICATION

This application is a divisional application of application Ser. No. 11/779,354, filed on 20 Apr. 2007.

FIELD OF THE INVENTION

This invention relates to implantable medical devices fabricated from polymers with radiopaque polymers.

BACKGROUND

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. The stent may be visualized during delivery and deployment using X-Ray fluoroscopy if it contains radiopaque materials.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Potential problems with polymeric implantable medical devices, such as stents, include insufficient toughness, slow degradation rate, and limited shelf life due to physical aging and stress relaxation. Another problem with polymeric stents is that polymer tend to be radiolucent, and thus cannot be visualized with X-ray fluoroscopy.

SUMMARY OF THE INVENTION

Various embodiments of the present invention include a stent formed from a biodegradable polymer material, wherein radiopaque functional groups are chemically bonded to at least some of polymers of the polymer material.

Further embodiments of the present invention include an implantable medical device comprising structural elements fabricated at least in part from a polymer blend comprising: a biodegradable matrix polymer blended with biodegradable linear block copolymers, the linear block copolymers having a discrete phase segment and a continuous phase segment, wherein the discrete phase segment is immiscible with the matrix polymer such that discrete phase segments form a discrete phase within the matrix polymer, wherein the continuous phase segment is miscible with the matrix polymer, wherein radiopaque functional groups are chemically bonded to the discrete phase segments, the continuous phase segments, or both.

Additional embodiments of the present invention include an implantable medical device comprising structural elements fabricated at least in part from a polymer blend comprising: a biodegradable matrix polymer blended with biodegradable star-block copolymers, the star-block copolymers having at least three arms, wherein the arms include inner segments and outer segments, the inner segments being immiscible with the matrix polymer and forming a discrete phase within the matrix polymer, wherein the outer segments are miscible with the matrix polymer, wherein radiopaque functional groups are chemically bonded to the inner segments or the outer segments.

DETAILED DESCRIPTION

Various embodiments of the present invention include an implantable medical device formed from a polymeric material including a polymer having radiopaque functional groups. In some embodiments, the radiopaque functional groups provide sufficient radiopacity to the polymeric material so that the device can be imaged by X-ray fluoroscopy.

As used herein, an "implantable medical device" includes, but is not limited to, self-expandable stents, balloon-expandable stents, stent-grafts, other expandable tubular devices for various bodily lumen or orifices, implantable cardiac pacemakers and defibrillators, leads and electrodes for the preceding, vascular grafts, grafts, artificial heart valves, and cerebrospinal fluid shunts. An implantable medical device can be designed for the localized delivery of a therapeutic agent. A medicated implantable medical device may be constructed by coating the device or substrate with a coating material containing a therapeutic agent. The substrate of the device may also contain a therapeutic agent.

Figure 1:
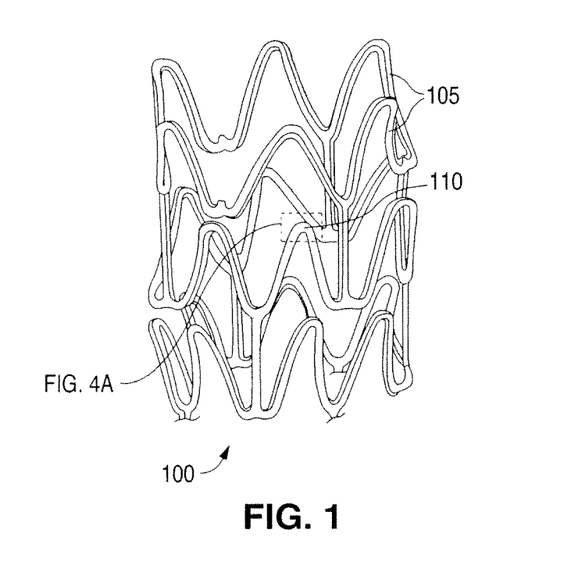
FIG. 1 depicts a view of a stent.

FIG. 1 depicts a view of a stent 100. In some embodiments, a stent may include a pattern or network of interconnecting structural elements 105. Stent 100 may be formed from a tube (not shown). The pattern of structural elements 105 can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

An implantable medical device can be made partially or completely from a biodegradable, bioabsorbable, biostable polymer, or a combination thereof. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

There are several characteristics that are important for implantable medical devices, such as stents, including high radial strength, good fracture toughness, fast degradation, and radiopacity. Some polymers that may be suitable for use in implantable medical devices have potential shortcomings with respect to these characteristics, in particular, fracture toughness and degradation rate.

Some crystalline or semi-crystalline polymers that are glassy or have a Tg above body temperature are particularly attractive as stent materials due to their strength and stiffness. The toughness of such polymers can be lower than desired, in particular, for use in stent applications. For example, polymers such as PLLA are stiff and strong, but tend to be brittle under physiological conditions. Physiological conditions refer to conditions that an implant is exposed to within a human body. Physiological conditions include, but are limited to, human body temperature, approximately 37° C. These polymers can exhibit a brittle fracture mechanism at these conditions in which there is little or no plastic deformation prior to failure. As a result, a stent fabricated from such polymers can have insufficient toughness for the range of use of a stent.

Furthermore, some biodegradable polymers have a degradation rate that is slower than desired for certain stent treatments. As a result, the degradation time of a stent made from such polymers can be longer than desired. For example, a stent made from a semicrystalline polymer such as PLLA can have a degradation time between about two and three years. In some treatment situations, a shorter degradation time is desirable, for example, less than 6 months or a year.

Additionally, polymers generally do not possess sufficient radiographic density to be easily imaged by fluoroscopy. Since a device such as a stent also has specific mechanical requirements, it is important that rendering a polymeric stent sufficiently radiopaque for imaging does not significantly impact its mechanical behavior. One way to improve the imaging of polymeric materials is to incorporate radiopaque filler materials into a polymeric material to enhance radiographic density. However, such materials may adversely affect the mechanical properties of the polymer, such as strength and toughness.

An alternative to filler materials is to fabricate a stent from polymers having radiopaque dye or functional group covalently bonded to the polymer backbone end groups. It is believed that the radiopaque density of the stent can be enhanced by the radiopaque functional groups without significantly impacting mechanical properties of the stent. Embodiments of the present invention include a stent formed from a biodegradable polymer material in which radiopaque functional groups are chemically bonded to at least some of polymers of the polymer material.

A radiopaque functional group can be any chemical group or species that can be bonded to a polymer backbone that increases or enhances the radiographic density of the polymer. Representative examples of radiopaque functional groups include iodine, triiodobenzoyl chloride, and triiodobenzoic acid.

A radiopaque functional group can be added to the end of a polymer or along the backbone of the polymer. A radiopaque functional group can be added to the end of an aliphatic polyester through an esterification reaction. In this reaction, a radiopaque group is substituted for a proton of a hydroxyl end group. Radiopaque agents such as triethyl amine and triidobenzoyl chloride are added to a polymer solution to allow an esterification reaction to occur. Exemplary synthesis schemes are provided herein.

Additionally, radiopaque groups can be covalently bonded to the backbone of some aliphatic polyesters. Biomaterials, 27 (2006) 4948-4954. It has been shown that iodine can be added to the backbone poly(caprolactone) by the removal of a proton of the methylene group in a position of the ester carbonyl. It is believed that such a scheme can be generally applied to aliphatic polyesters having such methylene groups. These include, but are limited to, poly (tetramethyl carbonate) (PTMC), poly(4-hydroxy butyrate), and polydioxanone. Exemplary synthesis schemes are provided herein.

In some embodiments, a majority of stent can be formed from an unbranched biodegradable polymer. In such embodiments, the unbranched polymer can be a sem-crystalline polymer such as poly(L-lactide) (PLLA), polyglycolide (LPLG), poly(tetramethyl carbonate) (PTMC), poly (4-hydroxy butyrate), polydioxanone, and copolymers thereof, or some other hydrolytically degradable semicrystalline polymer. The radiopaque functional groups may be chemically bonded to one or more of the ends of at least some of the polymers of the polymer material. Additionally or alternatively, the radiopaque functional groups can be chemically bonded along chains of at least some of the polymers of the polymer material. For example, a poly (lactide-co-caprolactone) copolymer can have radiopaque groups along the backbone bonded to the caprolactone groups. A polymer can include an amount of radiopaque functional groups that provide a sufficient degree of radiopacity to image the stent.

Figure 2:
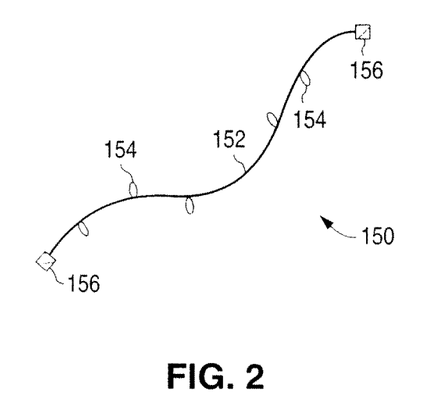
FIG. 2 depicts an unbranched polymer with radiopaque functional groups.

FIG. 2 depicts a schematic illustration of an unbranched polymer 150 with chemically bonded radiopaque functional groups. Polymer 150 has radiopaque groups 154 along its backbone 152 and radiopaque groups 156 endcapping backbone 152.

In further embodiments, a stent can be formed at least in part of star polymers. A star polymer is a polymer with at least three polymer chains or arms radiating from a center. The radiopaque functional groups can be chemically bonded to one or more of the ends of the arms of the star polymers. Additionally or alternatively, the radiopaque functional groups can be bonded along the chains of the arms of the star polymer. In an embodiment, a stent can be formed at least in part of biodegradable polymer material that is a blend of an unbranched polymer and a star copolymer with radiopaque functional groups chemically bonded to the star copolymer.

Figure 3:
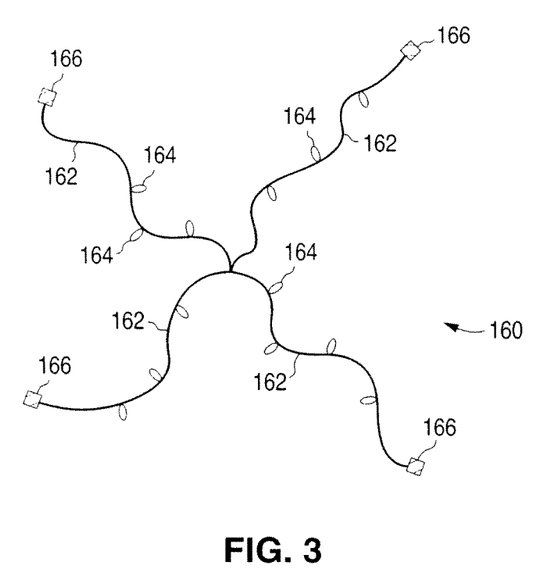
FIG. 3 depicts a star polymer with radiopaque functional groups.

FIG. 3 depicts a star polymer 160 chemically bonded with radiopaque functional groups. Star polymer 160 has four arms 162. Radiopaque groups 164 are chemically bonded along the chain of arms 162. Radiopaque groups 166 endcap arms 162. Radiopaque functional groups can be added to the unbranched or star polymers through the synthesis schemes described above.

Further embodiments of the present invention address all three of the potential shortcomings discussed above, inadequate toughness, slow degradation rate, and lack of radiopacity. One way to form a tougher polymeric material from a brittle polymer is to form a polymer blend including the brittle polymer and another polymer that has a higher fracture toughness than the brittle polymer. The higher toughness polymer should also be immiscible with or form a separate phase from the brittle polymer. For example, the higher toughness polymer can be a dispersed phase such that it forms discrete phase domains within the matrix polymer. The fracture toughness of a device is increased since the discrete phase can absorb energy arising from stress imparted to a device. To ensure good energy transfer between interfaces of the phases, it is important that there be sufficient bonding or adhesion between the phases. See, Y. Wang, etc. Journal of Polymer Science Part A: Polymer Chemistry, 39, 2001, 2755-2766. The dispersed phase should be interfacially compatible to reduce or eliminate formation of voids when the polymer blend is under stress, for example, when a stent is expanded.

Such further embodiments of the present invention include an implantable medical device fabricated at least in part from a polymer blend having a discrete or dispersed phase within a continuous phase. The polymer blend includes a matrix polymer blended with a block copolymer. At least one of the blocks, a discrete phase block, forms a discrete phase within the continuous matrix polymer phase since it is immiscible with the matrix polymer. At least another block, which is miscible with the matrix polymer, is within the continuous phase and provides interfacial bonding between the phases. Thus, these embodiments enhance the fracture toughness of a polymer for use in a stent. The block copolymer can be dispersed throughout the matrix polymer so that there is a plurality of discrete phase regions within the blend.

In some embodiments, the discrete phase can be faster degrading that the matrix polymer, and thus can provide a sufficiently fast degradation rate. The faster degradation can be due at least in part to the amorphous structure of the discrete phase since the diffusion rate of fluids through an amorphous structure is generally faster than through a crystalline structure.

In some embodiments, the matrix polymer has a high rigidity and a relatively low fracture toughness at physiological conditions. Such polymers may be selected as a matrix polymer for stent applications since such rigid polymers can support the walls of a vessel. The discrete phase segments can have a higher fracture toughness at physiological conditions, which can increase the toughness of the polymer blend. The continuous phase segments can improve adhesion between the continuous and discrete phases to facilitate energy transfer between the phases.

Figure 4A:
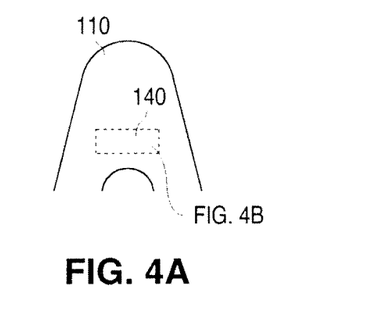
FIG. 4A depicts a section of a segment of a strut from the stent depicted in FIG. 1.
Figure 4B:
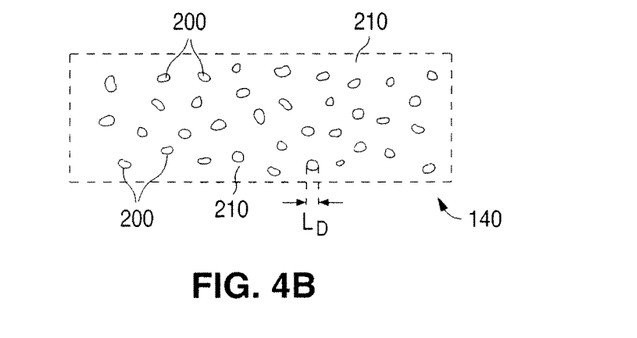
FIG. 4B depicts a microscopic schematic view of a portion of a segment of a strut as depicted in FIG. 4A

FIG. 4A depicts a section of a segment 110 of strut 105 from the stent depicted in FIG. 1. FIG. 4B depicts a microscopic schematic view of a portion 140 of segment 110 of a strut as depicted in FIG. 4A. Portion 140 includes a plurality of discrete phase regions 200 dispersed within a continuous phase 210. $L_D$ is a characteristic dimension of discrete phase region 200.

It is believed that when a device is placed under stress, the discrete phase tends to absorb energy when a fracture starts to propagate through a structural element. Crack propagation through the continuous phase may then be reduced or inhibited. As a result, fracture toughness of the polymer blend, and thus, the implantable medical device tends to be increased. The continuous phase segments of the block copolymer increase the adhesion between the discrete phase regions and the continuous phase. Thus, the discrete phase segments facilitate energy transfer between interfaces of the phases. Without the anchoring or adhesion provided by the continuous phase segments, a propagating crack may go around the discrete phase, reducing the effectiveness of the discrete phase in absorbing energy imparted to a device.

Generally, it is desirable for the discrete phase regions to be uniformly or substantially uniformly dispersed throughout the polymer matrix to facilitate the increase in toughness. The more dispersed the discrete phase regions, the greater is the increase in toughness. Additionally, the increase in toughness is related to the size of the discrete phase. Both the degree of dispersion and discrete phase size can be controlled by the length or molecular weight of the discrete phase inner segments. The characteristic length of a discrete phase can be 1 nm to 100 nm, 100 nm to 500 nm, 500 nm to 1,000 nm, 1000 nm to 10,000 nm, or greater than 10,000 nm. The molecular weight of the inner segments can be adjusted to obtain a desired characteristic length. For example, the molecular weight of the inner segments can be 10-50 kD, 50-100 kD, or higher than 100 kD.

In some embodiments, the block copolymer can be linear. In such embodiments, a biodegradable matrix polymer is blended with biodegradable linear block copolymers. Each of the linear block copolymers have one discrete phase segment and one continuous phase segment. The discrete phase segments form the discrete phase and the continuous phase segments are within the continuous matrix phase.

In some embodiments, the block copolymer can be a star block copolymer. In such embodiments, the polymer blend includes a matrix polymer blended with a star-block copolymer having at least three arms. In an embodiment, the arms include inner core segments that are discrete phase segments and outer segments that are continuous phase segments. The discrete phase inner segments are immiscible with the outer segments and the matrix polymer. The discrete phase inner segments form a discrete phase with the continuous phase which includes the matrix polymer and the outer segments.

In general, the continuous phase segments can be selected so that they are miscible with the matrix polymer. In some embodiments, the continuous phase segments can be the same chemical composition as the matrix polymer. For example, a polymer blend with a PLLA matrix polymer can have PLLA continuous phase segments.

In some embodiments, the discrete phase segments of a block copolymer include units that form polymers having a higher fracture toughness at physiological conditions than a rigid matrix polymer, such as PLLA. The discrete phase segments can form a discrete phase that is more flexible and has a lower modulus than the matrix polymer of the continuous phase. The matrix polymer can be selected to have a Tg above body temperature, so that the matrix polymer remains rigid after implantation. Generally, the discrete phase segments may be selected that have a Tg below body temperature. In one embodiment, the discrete phase segments of the block polymer can be a rubbery or elastomeric polymer. An "elastomeric" or "rubbery" polymer refers to a polymer that exhibits elastic deformation through all or most of a range of deformation. In some embodiments, the discrete phase can be substantially or completely amorphous.

Biodegradable polymers having a relatively high fracture toughness at body temperature include, but are not limited to, polycaprolactone (PCL), poly(tetramethyl carbonate) (PTMC), poly(4-hydroxy butyrate), and polydioxanone. Thus, some embodiments of the discrete phase segments of the block polymer can include caprolactone (CL), tetramethyl carbonate (TMC), 4-hydroxy butyrate, dioxanone units, or a combination thereof.

Radiopaque functional groups can be chemically bonded to the discrete phase segments or the continuous phase segments of the linear or star block copolymers to provide radiopacity to the device. The radiopaque functional groups can be bonded to the end groups of the continuous and discrete phase segments of the linear block copolymer. The radiopaque functional groups can also be bonded to the end groups of the continuous phase segments of the star block copolymer.

Figure 5:
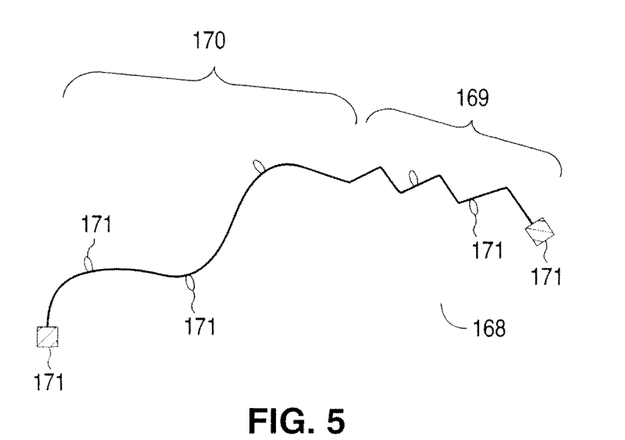
FIG. 5 depicts a linear block copolymer with radiopaque functional groups.
Figure 6:
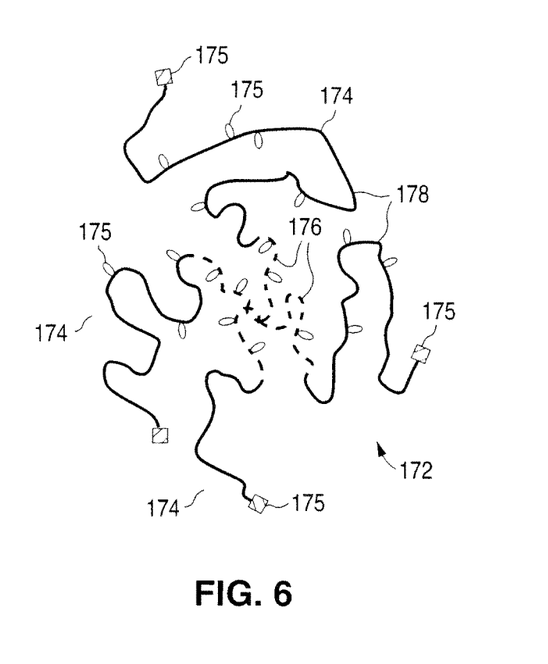
FIG. 6 depicts a star-block copolymer having four arms with radiopaque functional groups.

Additionally, the radiopaque functional groups can be bonded along the backbone of the continuous and discrete phase segments. For example, the continuous phase segments can include units such as CL, TMC, 4-hydroxy butyrate, and dioxanone that allow substitution of the radiopaque functional group for the proton of the methylene group in a position of the ester carbonyl. Further, such units can be included in the continuous phase segments to allow the same substitution. FIG. 5 depicts a linear block copolymer 168 with a discrete phase segment 169 and a continuous phase segment 170. Radiopaque functional groups 175 are bonded along discrete phase segments, continuous phase segments, and the ends of both segments FIG. 6 depicts a star-block copolymer 172 having four arms 174 with radiopaque functional groups 175. Arms 174 have discrete phase inner segments 176 (shown as broken lines) and continuous phase outer segments 178. Radiopaque functional groups 175 are bonded along inner segments, outer segments, and the ends of the outer segments.

In one embodiment, a polymer blend can have a PLLA matrix polymer with P(CL-co-TMC)-b-PLLA linear or star block copolymer dispersed within the PLLA matrix. The discrete phase segments are P(CL-co-TMC) and the continuous phase segments are PLLA. The PLLA continuous phase segments of the block copolymer are included within the continuous matrix phase. The PLLA continuous phase segments bind the discrete phase with the continuous phase, facilitating the increase in the fracture toughness provided to the polymer blend. In exemplary embodiments, the polymer blend can include about 1-30 wt %, or more narrowly, 5-20 wt % of a block copolymer and about 75-95 wt % of matrix polymer.

In additional embodiments, the block copolymer can include units in the discrete phase segments with characteristics that tend to increase the degradation rate of the blend. For example, the discrete phase inner segments can include units that are more hydrophilic than the matrix polymer. The discrete phase inner segments can also have units that are more hydrolytically active than the matrix polymer. These two characteristics increase the moisture content of the polymer blend which increases the degradation rate of the blend. Additionally, the discrete phase segments can also have units that have acidic and hydrophilic degradation products. Since the rate of the hydrolysis reaction tends to increase as the pH decreases, acidic degradation products can increase the degradation rate of the blend and the device. Glycolide (GA) units, for example, have acidic degradation products which can increase the degradation rate of a polymer blend when included in a discrete phase segment.

In some embodiments, the discrete phase segments can include units that increase the fracture toughness (toughness-enhancing units) of the polymer blend and units that have one or more of the characteristics that increase degradation rate mentioned above (fast degrading units). In an exemplary embodiment, the discrete phase segments can include both CL and GA units. In particular, the discrete phase inner segments can be poly(glycolide-co-ϵ-caprolactone) (P(GA-co-CL)). P(GA-co-CL) discrete phase segments can have alternating or random GA and CL units.

An exemplary block copolymer for blending with PLLA can include PLLA-b-P(CL-co-GA). The faster degrading GA units can increase the degradation rate of the polymer blend by increasing the equilibrium water content and penetration into the structural element. Degradation of GA units further increases the degradation rate due to the acidic and hydrophilic degradation products.

In some embodiments, the flexibility and degradation rate of the discrete phase segments can be adjusted by the ratio of fast degrading and toughness-enhancing units. As the ratio of CL, for example, increases in P(GA-co-CL) segments, the a block copolymer becomes more flexible and tougher. The Tg of the discrete phase segments can be tuned to a desired value by adjusting the ratio of component monomers. For example, the Tg of the discrete phase may be engineered to be less than a body temperature to provide a more flexible discrete phase under physiological conditions. Additionally, the degradation rate of the discrete phase segments, and thus the blend, can be increased by increasing the fraction of GA in the discrete phase segments. In exemplary embodiments, the P(GA-co-CL) segments can have up to 1 wt %, 5 wt %, 20 wt %, 50 wt %, 70 wt %, 80 wt %, or 90 wt % GA units.

In an exemplary embodiment, a polymer blend can have a PLLA matrix polymer with P(GA-co-CL)-b-PLLA block copolymer dispersed within the PLLA matrix. The discrete phase segments are P(GA-co-CL) and the continuous phase segments are PLLA. The PLLA continuous phase segments of the block copolymer phase separate into the PLLA matrix of the continuous matrix phase. The PLLA continuous phase segment binds the discrete phase with the continuous phase, facilitating the increase in the fracture toughness provided to the polymer blend. In exemplary embodiments, the polymer blend can include about 1-30 wt %, or more narrowly, 5-20 wt % of block copolymer and about 75-95 wt % of matrix polymer.

In further embodiments, the matrix polymer can be a copolymer. In some embodiments, a matrix copolymer can be composed of a primary functional group and at least one additional secondary functional group. The copolymer matrix may be a random copolymer including the primary functional group and at least one additional secondary functional group. In an embodiment, the copolymer with at least one secondary functional group can have a higher degradation rate than a homopolymer composed of the primary functional group. A secondary functional group can have a greater affinity for water or be more hydrolytically active than the secondary functional group. The secondary functional group can have acidic and hydrophilic degradation products that enhance the degradation of the matrix polymer and polymer blend. Additionally, a copolymer matrix may have lower crystallinity, which also tends to increase degradation rate. In some exemplary embodiments, the weight percent of the secondary functional group in the copolymer can have up to 1%, 5%, 10%, 15%, 30%, 40%, or, at least about 50%. In some embodiments, the weight percent of the secondary function group can be greater than 50%.

In an exemplary embodiment, the matrix copolymer can be poly(L-lactide-co-glycolide) (LPLG). The primary functional group can be L-lactide and the secondary functional group can be GA. The weight percent of the GA in the copolymer can be up to 1%, 5%, 10%, 15%, 30%, 40%, or at least about 50%. In certain exemplary embodiments, the weight percent of the GA group can be adjusted so that the degradation time of a stent, can be less than 18 months, 12 months, 8 months, 5 months, 3 months, or more narrowly, less than 3 months.

Additionally, the continuous phase segments of the block copolymer can be selected so that the continuous phase segments are miscible with the matrix copolymer. In one embodiment, the continuous phase segment can have the same chemical composition as the matrix copolymer. In another embodiment, the continuous phase segment can have a composition different from the matrix copolymer, but close enough so that the continuous phase segment is miscible with the matrix polymer. In another embodiment, the continuous phase segments can have a composition different from the matrix polymer with the continuous phase segments being miscible with the matrix polymer.

In another exemplary embodiment, a polymer blend can have an LPLG matrix polymer with P(CL-co-TMC)-b-LPLG block copolymer dispersed within the LPLG matrix. The discrete phase segments are P(CL-co-TMC) and the continuous phase segments are LPLG. The LPLG continuous phase segments of the star-block copolymer phase separate into the LPLG matrix of the continuous matrix phase. The LPLG discrete phase segment binds the discrete phase with the continuous phase, facilitating the increase in the fracture toughness provided to the polymer blend. In exemplary embodiments, the polymer blend can include about 1-30 wt %, or more narrowly, 5-20 wt % of a block copolymer and about 75-95 wt % of matrix polymer.

In further exemplary embodiments, a polymer blend can have an LPLG matrix polymer with P(GA-co-CL)-b-LPLG block copolymer dispersed within the LPLG matrix. The discrete phase segments are P(GA-co-CL) and the continuous phase segments are LPLG.

Linear and star-block copolymers, such as P(CL-co-TMC)-b-PLLA, P(GA-co-CL)-b-PLLA, P(CL-co-TMC)-b-LPLG, or P(GA-co-CL)-b-LPLG, can be formed by solution-based polymerization. Radiopaque functional groups can be added to the copolymers after formation of the copolymers. A radiopaque compound such as triiodobenzoyl chloride can be added to a solution containing the formed copolymers to allow an esterification reaction to proceed which chemically bonds the radiopaque functional groups to the copolymer. Other methods of forming the block copolymers are also possible, such as, without limitation, melt phase polymerization.

One embodiment of the solution polymerization involves forming the discrete phase segments first and then the continuous phase segments. The discrete phase monomers are combined with an appropriate solvent along with an appropriate initiator and catalyst to form the discrete phase segments. The continuous phase monomers and catalyst are then added to the solution to form the continuous phase blocks.

For example, to prepare P(GA-co-CL)-b-PLLA linear block copolymer, P(GA-co-CL) segments are formed first by mixing GA and CL monomers with a xylene solvent to form a solution which includes dodecanol as initiator and stannous octoate as catalyst. L-lactide monomers can then be added to the solution. The L-lactide monomers react with P(GA-co-CL) to form P(GA-co-CL)-b-PLLA.

Biodegradable multi-arm star-block copolymers can be synthesized through ring opening polymerization. J. Biomater. Sci. Polymer Edn., Vol. 17, 2006, 615-630. To prepare P(CL-co-TMC)-b-PLLA star-block copolymer, a precursor P(CL-co-TMC) star copolymer may be prepared first by solution polymerization. The P(CL-co-TMC) star copolymer is then employed as a macro-initiator to initiate the polymerization of L-lactide monomers to form the PLLA outer segments. Specifically, P(CL-co-TMC) star copolymer is formed first by mixing glycerol initiator, stannous octoate catalyst, CL units, and TMC units with a xylene solvent to form a solution. In the solution, the glycerol, CL, and TMC units react to form a three arm P(GA-co-CL) star copolymer.

L-lactide monomers are added to the solution and react with P(CL-co-TMC) star copolymer to form P(CL-co-TMC)-b-PLLA star-block copolymer.

To prepare P(GA-co-CL)-b-PLLA star-block copolymer, precursor P(GA-co-CL) star copolymer is formed first in a solution containing a solvent with GA units, CL units, pentaerythritol initiator, and stannous octoate catalyst. L-lactide monomers are then added to the solution to react with P(GA-co-CL) star copolymer to form P(GA-co-CL)-b-PLLA star block copolymer.

To prepare P(CL-co-TMC)-b-LPLG star-block copolymer, precursor P(CL-co-TMC) star copolymer is formed first in a solution containing a solvent with CL units, TMC units, glycerol initiator, and stannous octoate catalyst. L-lactide and GA units are then added to the solution to react with P(CL-co-TMC) star copolymer to form P(CL-co-TMC)-b-LPLG star-block copolymer.

Following each of these synthesis schemes, radiopaque functional groups can be added to the synthesized block copolymers as described above and in the examples below.

The solvent(s) can be selected so that the block copolymer precursor is soluble in the solvent(s) to enable the precursor copolymer to copolymerize with continuous phase segment units.

In other embodiments, block copolymers can be formed by reacting precursor discrete phase segments swollen with a solvent that contain continuous phase units. The precursor copolymer is swollen by a solvent after it is formed so that it can react with continuous phase units. One of skill in the art can select a solvent that swells but does not dissolve the precursor segments In one embodiment, the solvent for use in synthesizing the copolymer is devoid of alcohol functional groups. Such alcohol groups may act as initiators for chain growth in the polymer. Solvents used to synthesize the star-block copolymer include, but are not limited to, chloroform, toluene, xylene, and cyclohexane.

In some embodiments, the polymer blend of the matrix polymer and the block copolymer can be formed by solution blending, melt blending, or a combination thereof. The matrix polymer can be co-extruded with the polymer blend. The extruded polymer blend may be formed into a polymer construct, such as a tube or sheet which can be rolled or bonded to form a construct such as a tube. An implantable medical device may then be fabricated from the construct. For example, a stent can be fabricated from a tube by laser machining a pattern in to the tube. In another embodiment, a polymer construct may be formed from the polymer blend using an injection molding apparatus.

In some embodiments, the radiopacity of a stent can be enhanced by including a radiopaque layer in addition to a substrate or scaffolding composed primarily or completely of the polymer blend described herein. In such embodiments, the additional radiopaque layer can be an outer layer. The additional layer can be composed primarily or completely of block copolymer with radiopaque functional groups. The polymer blend layer can serve as a substrate or scaffolding that provides structural support and the block copolymer layer can serve primarily as a radiopaque layer.

In an embodiment, a two layer stent can be formed from a two layer tube with one layer being the polymer blend and another layer being the block copolymer with radiopaque functional groups. Such a tube can be formed through coextrusion of the polymer blend with a block copolymer. Two or more additional radiopaque layers are also possible.

In other embodiments, the additional radiopaque layer can be a coating over a scaffolding or substrate composed of the polymer blend.

In general, representative examples of polymers that may be used in embodiments of the present invention include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly (glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. For the purposes of the present invention, the following terms and definitions apply:

For the purposes of the present invention, the following terms and definitions apply:

The "glass transition temperature," Tg, is the temperature at which the amorphous domains of a polymer change from a brittle vitreous state to a solid deformable, ductile, or rubbery state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force at very low strain where the stress-strain curve is linear. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

Synthesis of P(GA-co-CL)-b-PLLA Star Copolymer with End Capped Radiopaque Groups The following example illustrates the synthesis of a multi-arm star copolymer, PLLA-b-P(GA-co-CL) with radiopaque end groups. In this example the following are used: CL, GA, and LLA as monomers; stannous octoate as catalyst; xylitol as initiator; and xylene as solvent. The proposed synthesis is as follows:

Step 1: 30 g GA, 20 g CL, 0.5 g xylitol, and 100 ml xylene are added into a reactor free of moisture and oxygen.

Step 2: 100 mg stannous octoate are added after the temperature has increased to 100° C. The solution will become very viscous.

Step 3: Approximately 72 h later, 25 g LLA and 0.14 ml catalyst are added.

Step 4: Approximately 48 h later, 100 ml xlyene, 20 ml of triethyl amine and 50 g triiodobenzoyl chloride are added for 2 h esterification reaction.

Step 5: The final product can be precipitated into methanol and dried in a vacuum oven overnight.

Example 2

Synthesis of P(GA-co-CL)-b-PLLA Star Copolymer with Radiopaque Side Groups and End Groups— Addition of Radiopaque Side Groups onto P(GA-co-CL)-b-PLLA Star Copolymer with Radiopaque End Groups Step 1: 100 g P(GA-co-CL)-b-PLLA star copolymer with radiopaque end groups (from Example 1) is dissolved in 2 L anhydrous THF in a reactor equipped with a mechanical stirrer and the solution is kept at low temperature (−70° C.) under argon atmosphere.

Step 2: 300 mL lithium diisopropyl amide solution in THF (2M/L) is added into the reactor and the mixture is stirred for 1 h.

Step 3: 150 g iodine (in 200 mL THF) is added into the reactor and the mixture is stirred for 2 h.

Step 4: The star copolymer with formed iodine side groups is extracted with 5 L dichloromethane.

Step 5: The dichloromethane solvent is partially evaporated under reduced pressure. Then the concentrated star copolymer solution is precipitated into 5 L methanol, filtered out, and dried under vacuum at 80° C. till constant weight.

Example 3

The following example illustrates the preparation of PLLA with radiopaque end group(s):

Step 1: Dissolve 500 g PLLA into 5 L xylene. Then add 13 ml of triethyl amine and 40 g triiodobenzoyl chloride for 2 h esterification reaction.

Step 2: The final product can be precipitated into methanol and dried in a vacuum oven overnight.

Example 4

The following example illustrates stent preparation from the blend of PLLA/radiopaque block copolymer:

Step 1: A two layer tubing is formed by the coextrusion of a PLLA/radiopaque star block copolymer blend (100:10) as inner layer and radiopaque star block copolymer as outer layer. The thickness of inner layer and the radiopaque outer layer is set to 0.05 inch and 0.005 inch, respectively. The ID of the extruded tubing is set to about 0.021 inch and the OD is about 0.076 inch.

Step 2: Expand the extruded tubing and cut into stent by laser.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device comprising structural elements fabricated at least in part from a polymer blend comprising:
a biodegradable matrix polymer blended with biodegradable star-block copolymers, the star-block copolymers having at least three arms, wherein the arms include inner segments and outer segments, the inner segments being immiscible with the matrix polymer and forming a discrete phase within the matrix polymer, wherein the outer segments are miscible with the matrix polymer, wherein radiopaque functional groups are chemically bonded to the inner segments or the outer segments.

2. The device of claim 1, wherein the implantable medical device is a stent.

3. The device of claim 1, wherein the radiopaque functional groups are selected from the group consisting of iodine, triiodobenzoyl chloride and triiodobenzoic acid.

4. The device of claim 1, wherein the radiopaque functional groups are chemically bonded to one or more of the ends of the outer segments.

5. The device of claim 1, wherein the radiopaque functional groups are chemically bonded along the backbone of the inner segments.

6. The device of claim 5, wherein the radiopaque functional group is added by removal of a proton of a methylene group in an α-position of an ester carbonyl on the backbone.

7. The device of claim 1, wherein the star-block copolymers are dispersed throughout the matrix polymer.

8. The device of claim 1, wherein the inner segments are faster degrading than the outer segments.

9. The device of claim 1, wherein the outer segments are of the same or similar chemical composition as the matrix polymer.

10. The device of claim 1, wherein the inner segments have a Tg below body temperature so that the discrete phase is elastic at physiological conditions, and wherein the outer segments and the matrix polymer have a Tg above body temperature so that the continuous phase is glassy at physiological conditions.

11. The device of claim 1, wherein the matrix polymer and the outer segments comprise PLLA.

12. The device of claim 1, wherein the inner segments comprise units selected from the group consisting of CL, TMC, and dioxanone.

13. The device of claim 1, wherein 1 to 20 wt % of the polymer blend comprises the star-block copolymer.

14. The device of claim 1, wherein the structural elements comprise a first layer comprising the polymer blend and a second layer comprising a majority of the star block copolymer including the radiopaque functional groups chemically bonded to the inner segments, the outer segments, or both.

* * * * *